US011832659B1

(12) United States Patent
Solotoff

(10) Patent No.: US 11,832,659 B1
(45) Date of Patent: Dec. 5, 2023

(54) THERAPEUTIC SHIRT WITH HIGH COMPRESSION MATERIAL POSITIONED OVER EXTERNALLY ACCESSED POCKETS HOUSING CUSTOM HEAT/COLD PACKS

(71) Applicant: PREFERRED PRESCRIPTION, INC., Hollywood, FL (US)

(72) Inventor: Brandon Solotoff, Boca Raton, FL (US)

(73) Assignee: Preferred Prescription, INC., Hollywood, FL (US)

(*) Notice: Subject to any disclaimer, the term of this patent is extended or adjusted under 35 U.S.C. 154(b) by 88 days.

(21) Appl. No.: 17/089,907

(22) Filed: Nov. 5, 2020

Related U.S. Application Data

(63) Continuation-in-part of application No. 17/020,072, filed on Sep. 14, 2020, and a continuation-in-part of application No. 17/008,734, filed on Sep. 1, 2020.
(Continued)

(51) Int. Cl.
*A41D 13/00* (2006.01)
*A41B 1/08* (2006.01)
(Continued)

(52) U.S. Cl.
CPC ............ *A41D 13/0015* (2013.01); *A41B 1/08* (2013.01); *A41D 27/02* (2013.01); *A41D 27/085* (2013.01);
(Continued)

(58) Field of Classification Search
CPC .. A41D 13/0015; A41D 31/185; A41D 27/02; A41D 27/085; A41D 27/20;
(Continued)

(56) References Cited

U.S. PATENT DOCUMENTS

| 114,615 | A | | 5/1871 | Smitley |
| 395,729 | A | * | 1/1889 | Whaley ................. A41D 27/20 |
| | | | | 2/248 |

(Continued)

FOREIGN PATENT DOCUMENTS

| CA | 2838790 | 12/2012 |
| EP | 2430931 | 3/2012 |

(Continued)

OTHER PUBLICATIONS

"Study of Properties of Medical Compression Fabrics," Lijing Wang, et al., Journal of Fiber Bioengineering & Informatics, Global Science Press, p. 15-22 (2011).
(Continued)

*Primary Examiner* — Heather Mangine
*Assistant Examiner* — Raquel M. Weis
(74) *Attorney, Agent, or Firm* — Thomas A. O'Rourke; James Bongiorno

(57) ABSTRACT

A garment for treating (heating/cooling/compressing) one or more regions of a wearer's body includes a primary layer, particularly located layer/layers of higher compression materials, and a liner creating a pocket. An interior surface of the primary layer, an elastic, applies a first level of compression to a portion of the wearer's body, including the treatment region(s). The layer(s) of higher compression material(s) on the interior surface of the primary layer overlay and extend beyond the treatment region(s), applying a second, higher level of compression. The primary layer has an opening adjacent to the higher compression material(s). A first peripheral portion of the liner is secured to the interior of the primary layer and extends over the opening, with a second peripheral portion extending over only a portion of a periphery of the higher compression material(s), being
(Continued)

secured thereto to form a gonfalon-shaped pocket that receives a correspondingly shaped heat/cold pack.

17 Claims, 10 Drawing Sheets

Related U.S. Application Data

(60) Provisional application No. 62/934,591, filed on Nov. 13, 2019, provisional application No. 62/934,587, filed on Nov. 13, 2019, provisional application No. 62/911,495, filed on Oct. 7, 2019, provisional application No. 62/899,277, filed on Sep. 12, 2019.

(51) Int. Cl.
*A61F 7/02* (2006.01)
*A41D 27/02* (2006.01)
*A41D 27/08* (2006.01)
*A41D 31/18* (2019.01)
*A41D 27/20* (2006.01)

(52) U.S. Cl.
CPC ............ *A41D 27/20* (2013.01); *A41D 31/185* (2019.02); *A61F 7/02* (2013.01); *A61F 2007/0238* (2013.01)

(58) Field of Classification Search
CPC ... A41D 13/0012; A41D 13/0058; A61F 7/02; A61F 2007/0238
See application file for complete search history.

(56) References Cited

U.S. PATENT DOCUMENTS

| | | | |
|---|---|---|---|
| 441,046 A * | 11/1890 | Wright | A41D 27/20 2/254 |
| 1,195,738 A * | 8/1916 | Rose | A41D 27/02 2/97 |
| 1,369,369 A * | 2/1921 | Walker | A41D 27/201 2/251 |
| 1,442,020 A * | 1/1923 | Wood | A41D 27/201 24/633 |
| 1,567,931 A | 12/1925 | Epler | |
| 1,578,712 A * | 3/1926 | Clark | A41D 27/201 24/481 |
| 1,970,081 A | 8/1934 | Eisendrath | |
| 2,403,676 A * | 7/1946 | Modlinski | A61F 7/02 2/84 |
| 2,648,325 A * | 8/1953 | Siple | A61F 7/02 607/104 |
| 3,338,236 A | 8/1967 | McLeod | |
| 3,476,102 A | 11/1969 | Sarnoff | |
| 3,882,873 A | 5/1975 | Arrango | |
| 3,950,789 A * | 4/1976 | Konz | F25D 3/14 2/81 |
| 4,033,354 A | 7/1977 | De Rosa | |
| 4,190,054 A | 2/1980 | Brennan | |
| 4,204,543 A | 5/1980 | Henderson | |
| 4,384,369 A * | 5/1983 | Prince | A63B 21/065 2/81 |
| 4,470,417 A | 9/1984 | Gruber | |
| 4,480,637 A | 11/1984 | Florek | |
| 4,676,247 A | 6/1987 | Van Cleve | |
| 4,688,572 A | 8/1987 | Hubbard | |
| 4,856,294 A | 8/1989 | Scaringe | |
| 4,972,832 A | 11/1990 | Trapini | |
| 5,005,374 A | 4/1991 | Spitler | |
| 5,018,521 A * | 5/1991 | Campbell | A61F 7/02 607/98 |
| 5,020,711 A | 6/1991 | Kelley | |
| 5,038,779 A * | 8/1991 | Barry | A41D 13/0058 607/108 |
| 5,072,455 A * | 12/1991 | St. Ours | A41D 13/0058 2/92 |
| 5,072,598 A | 12/1991 | Dibrell | |
| 5,146,625 A * | 9/1992 | Steele | A41D 13/0058 2/92 |
| 5,148,804 A | 9/1992 | Hill | |
| 5,302,806 A * | 4/1994 | Simmons | A42B 3/285 607/108 |
| 5,388,271 A * | 2/1995 | Sessoms | A41D 13/0015 2/113 |
| 5,466,251 A | 11/1995 | Brunson | |
| 5,468,152 A * | 11/1995 | Lenart | A41D 27/08 2/247 |
| 5,536,246 A | 7/1996 | Saunder | |
| 5,555,566 A * | 9/1996 | Kuhn | A41D 27/20 2/108 |
| 5,628,725 A | 5/1997 | Ostergard | |
| 5,636,380 A | 6/1997 | Schindler | |
| 5,787,505 A * | 8/1998 | Piwko | A41D 13/0058 2/247 |
| 5,826,273 A * | 10/1998 | Eckes | A41D 13/0051 2/69 |
| 5,857,990 A | 1/1999 | Maas | |
| 5,901,373 A * | 5/1999 | Dicker | A41D 31/125 2/243.1 |
| 5,937,442 A | 8/1999 | Yamaguchi | |
| 6,189,153 B1 * | 2/2001 | Diamond | A41D 27/20 2/248 |
| 6,306,111 B1 | 10/2001 | Dean | |
| 6,440,094 B1 | 8/2002 | Maas | |
| 6,598,235 B2 | 7/2003 | Bulla | |
| 6,709,411 B1 | 3/2004 | Olinger | |
| 7,246,381 B2 | 7/2007 | Green | |
| 7,631,368 B1 * | 12/2009 | Samson | F41C 33/02 2/77 |
| 7,871,388 B2 | 1/2011 | Brown | |
| 8,047,893 B2 | 11/2011 | Fenske | |
| 8,172,782 B2 | 5/2012 | Rock | |
| 8,214,926 B2 | 7/2012 | Brown | |
| 8,220,074 B2 * | 7/2012 | Sutker | A41D 13/0058 2/69 |
| 8,256,034 B2 * | 9/2012 | Berner, Jr. | A41D 31/185 2/455 |
| 8,434,163 B1 * | 5/2013 | Nudo | A41D 13/0051 2/22 |
| 8,533,864 B1 * | 9/2013 | Kostrzewski | A41D 13/0015 2/69 |
| 8,597,222 B2 * | 12/2013 | Lucero | A41D 27/20 602/62 |
| 8,827,767 B2 * | 9/2014 | Samoodi | A41C 1/10 450/20 |
| 8,876,875 B1 * | 11/2014 | Nilforushan | A61H 1/008 607/108 |
| 8,905,956 B2 * | 12/2014 | Waeger | A61F 5/026 128/846 |
| 8,910,317 B2 * | 12/2014 | Decker | A41D 31/185 602/19 |
| 9,167,854 B2 | 10/2015 | Levian | |
| 9,339,065 B2 * | 5/2016 | Willis | A41D 13/0058 |
| 9,370,440 B2 | 6/2016 | Ingimundarson | |
| 9,572,705 B2 | 2/2017 | Ingimundarson | |
| 9,598,794 B2 * | 3/2017 | Isanhart | A41D 13/0012 |
| D793,570 S | 8/2017 | Sherman | |
| 9,775,392 B2 * | 10/2017 | Peterson | A41D 27/204 |
| 9,883,703 B2 | 2/2018 | Schultz | |
| 9,980,526 B2 | 5/2018 | Silverberg | |
| D838,932 S | 1/2019 | Lawler | |
| 2001/0054193 A1 * | 12/2001 | Stembridge | A41D 13/0015 2/69 |
| 2002/0092312 A1 | 7/2002 | Head | |
| 2002/0100108 A1 * | 8/2002 | Stuart | A41D 13/0015 2/247 |
| 2004/0083529 A1 * | 5/2004 | Tate | A41D 13/0015 2/115 |
| 2004/0132367 A1 * | 7/2004 | Rock | A41D 27/04 442/79 |
| 2006/0218692 A1 | 10/2006 | Lamarque | |

(56) References Cited

U.S. PATENT DOCUMENTS

| | | | |
|---|---|---|---|
| 2006/0253954 A1* | 11/2006 | Music | A41D 13/0051 2/115 |
| 2006/0276089 A1* | 12/2006 | Amarasinghe | A41D 13/0058 428/72 |
| 2007/0299489 A1* | 12/2007 | Francis, Jr. | A41D 31/12 607/108 |
| 2008/0033517 A1* | 2/2008 | Scheberle | A41D 13/1245 607/108 |
| 2008/0040831 A1* | 2/2008 | Nilforushan | A61F 7/02 219/211 |
| 2008/0125842 A1* | 5/2008 | Petitt | A61F 7/02 607/108 |
| 2008/0201818 A1* | 8/2008 | Nilforushan | A61F 7/02 607/114 |
| 2008/0208089 A1 | 8/2008 | Newkirk | |
| 2008/0209932 A1* | 9/2008 | Clarke | A41D 13/0053 607/108 |
| 2008/0256690 A1* | 10/2008 | Grilliot | A41D 13/0012 2/455 |
| 2009/0062704 A1 | 3/2009 | Brown | |
| 2010/0017934 A1* | 1/2010 | Guelzow | A41D 13/0015 2/93 |
| 2010/0024101 A1* | 2/2010 | Berner, Jr. | A41D 13/0015 2/243.1 |
| 2010/0031416 A1* | 2/2010 | Grilliot | A41D 13/01 2/102 |
| 2010/0089897 A1* | 4/2010 | Bart | A61F 7/034 2/243.1 |
| 2010/0144490 A1* | 6/2010 | Purdy | A63B 21/4007 2/69 |
| 2010/0242158 A1* | 9/2010 | Blakely | A41D 13/0512 2/461 |
| 2011/0041229 A1* | 2/2011 | Niemi | A41D 19/01535 607/108 |
| 2011/0145980 A1* | 6/2011 | D'Alessandro | A41D 27/20 2/254 |
| 2011/0185471 A1* | 8/2011 | Buczkowski | A41D 27/20 2/84 |
| 2011/0203034 A1* | 8/2011 | Shlafer | A41D 27/208 2/247 |
| 2011/0214216 A1* | 9/2011 | Zarabi | A41F 9/00 2/69 |
| 2011/0219520 A1 | 9/2011 | Roland | |
| 2011/0274903 A1* | 11/2011 | Stuart | C08L 75/04 501/32 |
| 2011/0302686 A1* | 12/2011 | Chapuis | A41D 13/0015 2/242 |
| 2012/0078147 A1* | 3/2012 | Ogulnick | A61F 13/143 602/2 |
| 2012/0090072 A1* | 4/2012 | Oprandi | A41D 13/1245 2/114 |
| 2012/0174282 A1* | 7/2012 | Newton | A41D 31/185 2/69 |
| 2013/0104280 A1* | 5/2013 | Boynton | A61F 5/026 2/69 |
| 2013/0220297 A1* | 8/2013 | Sivucka | A61F 7/034 126/204 |
| 2014/0012161 A1* | 1/2014 | Ross, Jr. | A41D 1/002 600/595 |
| 2014/0194961 A1* | 7/2014 | Evans, Jr. | A61F 7/106 607/112 |
| 2014/0238085 A1* | 8/2014 | Smith | A61F 13/08 66/175 |
| 2014/0317826 A1* | 10/2014 | Decker | A41D 13/0015 2/69 |
| 2014/0336544 A1 | 11/2014 | Ransom | |
| 2014/0336556 A1* | 11/2014 | Pucik | A61F 5/02 602/19 |
| 2014/0358203 A1* | 12/2014 | Li | A61F 7/00 607/108 |
| 2015/0089707 A1* | 4/2015 | Walmsley | A41D 13/0058 2/69 |
| 2015/0096095 A1* | 4/2015 | Valenti | A41D 13/0058 2/24 |
| 2015/0237926 A1* | 8/2015 | Placanica | A41D 13/0015 2/115 |
| 2015/0296890 A1* | 10/2015 | Moloney | A41D 27/20 2/69 |
| 2015/0335472 A1* | 11/2015 | Li | A61F 7/02 607/108 |
| 2016/0015104 A1* | 1/2016 | Edwards | A24F 3/00 2/84 |
| 2016/0073715 A1* | 3/2016 | Fayed | A41D 27/20 2/253 |
| 2016/0198776 A1* | 7/2016 | Stevens | A41D 13/0058 219/211 |
| 2016/0206017 A1* | 7/2016 | Aylward | A41D 27/20 |
| 2016/0242474 A1* | 8/2016 | Baschak | A41D 31/102 |
| 2016/0249698 A1* | 9/2016 | Berzowska | A41D 13/1281 2/69 |
| 2016/0278963 A1* | 9/2016 | Webster | A61F 5/05858 |
| 2017/0027240 A1* | 2/2017 | McClean | A41D 1/14 |
| 2017/0135418 A1* | 5/2017 | Patton | A41B 7/06 |
| 2017/0156415 A1* | 6/2017 | Winner | A41D 13/1245 |
| 2017/0231798 A1 | 8/2017 | Shin | |
| 2017/0347729 A1* | 12/2017 | Goff | A41D 27/20 |
| 2018/0064182 A1* | 3/2018 | Brockway | A61F 13/085 |
| 2018/0064236 A1* | 3/2018 | Wolfe | A41D 27/20 |
| 2018/0085655 A1 | 3/2018 | Kasmark | |
| 2018/0228226 A1* | 8/2018 | Corcoran | A41D 31/18 |
| 2018/0228232 A1* | 8/2018 | Fisher | A41F 9/025 |
| 2018/0271192 A1* | 9/2018 | Parriott | A41D 27/20 |
| 2018/0317573 A1* | 11/2018 | Devito | H05B 3/342 |
| 2018/0338549 A1* | 11/2018 | Orr | H05B 3/36 |
| 2019/0000159 A1* | 1/2019 | Roberts | A61F 7/10 |
| 2020/0229523 A1* | 7/2020 | Polegato Moretti | A41D 27/06 |

FOREIGN PATENT DOCUMENTS

| | | |
|---|---|---|
| EP | 3315103 | 5/2018 |
| GB | 2504313 | 1/2014 |

OTHER PUBLICATIONS

"Compression Garments for Medical Therapy and Sports," Ying Xiong and Xiaoming Tao, Polymers, vol. 10, No. 663, 3-19, Jun. 14, 2018.

"From 3d Scan to Body Pressure of Compression Garments," Li Z, Malengier B, et al., AUTEX2019—19th World Textile Conf. on Textiles at the Crossroads, Jun. 11-15, 2019.

"Physics of Compression," Hugo Partsch, Published by Guset User, Nov. 24, 2015.

Bringing Light Into the Dark: Effects of Compression Clothing on Performance and Recovery, Dennis-Peter Born, International Journal of Sports Physiology and Performance, 2013.

Press Fit Forces Stress Design Calculator, Jun. 18, 2018, available at: www.engineersedge.com/calculators/machine-design/press-fit/press-fit.htm.

"Three General Types of Fit," available at www.mmto.org/dclark/Reports/Encoder%20Upgrade/fittolerences%20%5BRead-Only%5D.pdf., Jul. 8, 2019.

"Engineering Fit," available at: https://en.wikipedia.org/wiki/Engineering_fit, Jul. 8, 2019.

* cited by examiner

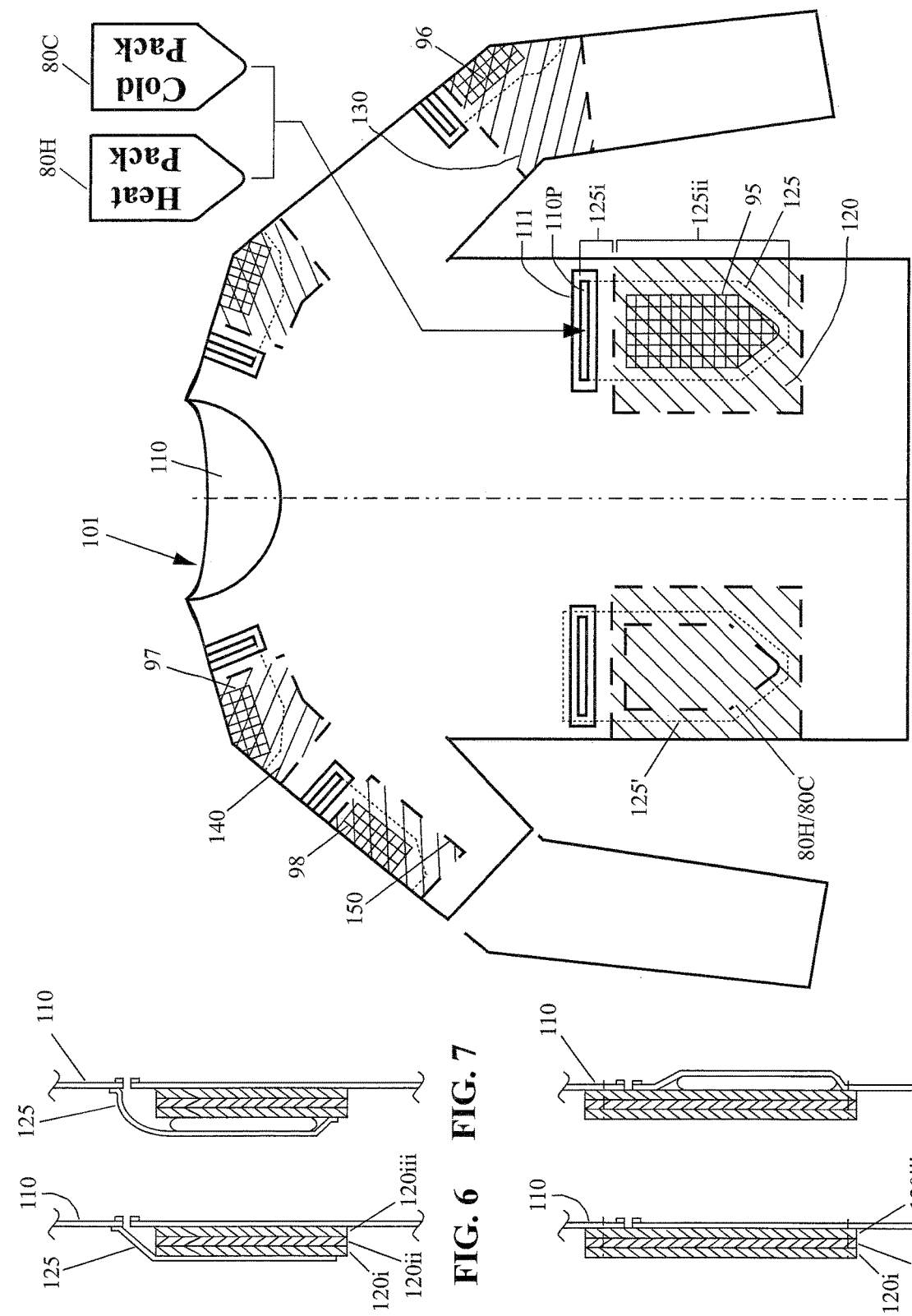

THERAPEUTIC SHIRT WITH HIGH COMPRESSION MATERIAL POSITIONED OVER EXTERNALLY ACCESSED POCKETS HOUSING CUSTOM HEAT/COLD PACKS

CROSS REFERENCES TO RELATED APPLICATIONS

This application claims priority on U.S. Provisional Application Ser. No. 62/934,591, filed on Nov. 13, 2019, and is a continuation in part of U.S. patent application Ser. No. 17/008,734, filed on Sep. 1, 2020, having the title "Therapeutic Shirt with High Compression Support for Improved Posture and Comfort for Pregnant Women and Overweight Wearers," which claims priority on U.S. Provisional Application Ser. No. 62/899,277 filed on Sep. 12, 2019; and this application is also a continuation in part of U.S. patent application Ser. No. 17/020,072, filed on Sep. 14, 2020, having the title "Compression Garments," which claims priority on U.S. Provisional Application Ser. No. 62/911,495, filed on Oct. 7, 2019, and U.S. Provisional Application Ser. No. 62/934,587, filed on Nov. 13, 2019, all disclosures of which are incorporated herein by reference.

FIELD OF THE INVENTION

The subject technology relates generally to compression and thermal therapy garments, and more particularly to a shirt configured with specially located high compression materials to provide targeted compression areas with pockets underneath those compression areas, which pockets receive heat/cold packs that are inserted externally while the garment is worn, to more effectively treat arm, rib, and shoulder injuries and to protect the rib cage of various different wearers, including, but not limited to, athletes such as football players.

BACKGROUND OF THE INVENTION

Compression garments are clothing items that may be worn to provide support in the form of compressive pressure applied to a particular region or regions of the wearer's body. Compression garments may be used by the wearer for therapeutic reasons and also for enhancing athletic performance during sporting events. In general, the use of various different pressures that may be achieved by compression fabrics with different engineered compression gradients for medical and athletic purposes has been studied. See e.g., "Study of Properties of Medical Compression Fabrics," Lijing Wang, Martin Felder, and Jackie Y. Cai, Journal of Fiber Bioengineering & Informatics, Global Science Press, p. 15-22 (2011); "Compression Garments for Medical Therapy and Sports," Ying Xiong and Xiaoming Tao, Polymers, Vol. 10, No. 663, 3-19, Jun. 14, 2018; "From 3d Scan To Body Pressure Of Compression Garments," Li Z, Malengier B, Vasile S, Cools J, Van Langenhove L, AUTEX2019—19th World Textile Conference on Textiles at the Crossroads, 11-15 Jun. 2019, Ghent, Belgium; "Physics of Compression," HUGO PARTSCH, Published by Guset User, 2015-11-24; and "Bringing Light Into the Dark: Effects of Compression Clothing on Performance and Recovery," Dennis-Peter Born, Billy Sperlich, and Hans-Christer Holmberg, International Journal of Sports Physiology and Performance, 2013, 8:4-18 (2013).

Examples of the use of compression garments for medical reasons include compression stockings for improving blood circulation, and treating varicose veins, edema, lymphedema, and deep vein thrombosis. Compression socks may be worn on a plane where a person is inactive and confined in a small space to reduce the risk of blood clots. Compression stockings and socks may also be worn by a person who must stand for long periods of time. Compression sleeves may also be worn on a person's legs to treat shin splints, muscle cramps, and tendonitis.

With respect to the compression garments being used to enhance athletic performance, such use helps the muscles to more quickly recover from previous strenuous activity. Scientific studies have shown that the wearing of a compression sleeve causes the walls of the wearer's arteries to dilate, thereby increasing the flow of blood to those muscles, providing more oxygen and nutrients that are needed, which also tends to reduce the build-up of lactic acid. The wearing of a compression sleeve may also serve to support the muscles and reduce muscular vibrations, reducing the fatigue that results from those vibrations, thereby improving athletic endurance.

Some compression garments for enhancing various aspects of the wearer may include, for example, the following U.S. Patent and Patent App. Pub. Nos.: U.S. Pat. No. 5,937,442 to Yamaguchi; U.S. Pat. No. 6,440,094 to Maas; U.S. Pat. No. 7,871,388 to Brown; U.S. Pat. No. 8,172,782 to Rock, U.S. Pat. No. 8,827,767 to Samoodi; U.S. Pat. No. 9,167,854 to Levian; 2009/0062704 (Brown); and 2012/0078147 (Ogulnick).

In addition, some garments have been adapted to apply thermal treatment (applications of heat/cold) to portions of the person's body, as shown for example by the following U.S. Patent and Patent App. Pub. Nos.: U.S. Pat. No. 5,826,273 to Eckes; U.S. Pat. No. 8,220,074 to Sutker; U.S. Pat. No. 8,256,034 to Berner; U.S. Pat. No. 8,876,875 to Niforushan; U.S. Pat. No. 9,339,065 to Willis; 2006/0218692 (Lamarque); 2007/0299489 (Francis); and 2008/0125842 (Petit).

One problem with many prior art devices is that they include straps that are unnecessarily confining and very uncomfortable, and many prior art compression garments are very unsightly, and typically cannot be worn without being seen because they are intended to be worn over the person's clothing.

Another problem with the prior art devices for applications of heat/cold is that the openings into the pockets are often positioned internal to the garment so that the heat/cold packs cannot be changed while being worn, and/or that the heat/cold packets are on the outside of the garment.

A therapeutic shirt is disclosed herein that provides targeted compression areas with pockets beneath those compression areas, which pockets receive heat/cold packs that may be easily inserted from the outside of the garment while it is being worn, for use in more effectively treating arm, rib, and shoulder injuries of the wearer, including those sustained by athletes such as football players.

The therapeutic shirt disclosed herein may also be worn beneath a regular shirt, such as a button down shirt or a pull-over shirt.

It is noted that citing herein of any patents, published patent applications, and non-patent literature is not an admission as to any of those references constituting prior art with respect to the herein disclosed and/or claimed apparatus.

OBJECTS OF THE INVENTION

It is an object of the invention to provide a compression garment in the form of a shirt that may be worn to improve the posture of a person.

It is another object of the invention to provide a compression garment in the form of a shirt that may be worn for treating rib injuries.

It is a further object of the invention to provide a compression garment in the form of a shirt that may be worn for treating shoulder injuries.

It is another object of the invention to provide a compression garment in the form of a shirt that may be worn for treating elbow and other arm injuries.

It is also an object of the invention to provide a compression garment in the form of a shirt that may be worn to protect and/or treat the wearer's rib cage.

It is another object of the invention to provide a compression garment in the form of a shirt that may be configured to provide heat and/or cold treatment to targeted areas of the wearer's body.

It is also an object of the invention to provide a compression garment in the form of a shirt that may be configured to provide high compression regions above pockets that are used to house heat/cold packs to more effectively provide heat and/or cold treatment to the wearer's body.

It is another object of the invention to provide a compression garment in the form of a shirt that may be configured to provide high compression regions above pockets that are used to house heat/cold packs to provide greater thermal efficiency and longevity with respect to the heating and cooling capability of the heat/cold packs.

It is a further object of the invention to provide custom shaped heat/cold packs that may more easily be inserted into pockets positioned beneath high compression materials.

It is another object of the invention to provide a gonfalon-shaped pocket interior that is sized to receive a corresponding gonfalon-shaped heat/cold packs therein.

Further objectives and advantages of the various garments disclosed herein will become apparent from the following description and claims, and from the accompanying drawings.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In accordance with at least one embodiment, a garment for selectively treating (i.e., heating or cooling) one or more regions of a wearer's body may include a primary layer of a first material, particularly located one or more layers of higher compression materials, and a liner creating a particularly formed pocket at the particularly located higher compression materials. The primary layer of the first material may be configured for an interior surface thereof to envelop a portion of the wearer's body including the one or more regions, and may thus be formed of an elastic material configured for the interior surface to apply a first level of compression to the portion of the wearer's body. The primary layer of elastic material may be formed of a spandex, a polyester blend, a bamboo blend, as well as any other suitable elastic material known in the art.

The one or more layers of higher compression materials may each be fixedly secured to the interior surface of the primary layer and be shaped to overlay and extend beyond the one or more treatment regions of the wearer's body. The one or more layers of higher compression materials may each be configured to apply a second level of compression, being higher than the first level of compression applied by the first material. In one embodiment the one or more layers of the higher compression material may be three layers that form an innermost layer, a middle layer, and an outermost layer. The one or more layers of higher compression material may utilize a thermoplastic elastomer (TPE) material, a polyurethane, or any other suitable material.

The primary layer includes an opening adjacent to the one or more layers of the higher compression material, with the opening being sized to admit a heat/cold pack therethrough. A portion of a periphery of the liner may be fixedly secured to the interior surface of the primary layer with the first portion of the liner being configured to extend over the opening, and a second portion of a periphery of the liner material may be configured to extend over only a portion of a periphery of the one or more layers of the higher compression material, and be secured thereto to form the pocket. The liner is formed with a particularly shaped periphery such that an interior of the pocket forms a gonfalon shape, with a tip of the gonfalon shape positioned at a lower position on the wearer. The tip of the gonfalon shape may preferably be rounded. The pocket is so shaped to receive a heat/cold pack therein that has a correspondingly shaped periphery. The opening in the primary layer, which may be an elongated slit, may be supported against tears and ripping through the use of a reinforcement material positioned about an entire periphery of the opening.

The reinforcement material positioned about the opening may be any suitable reinforcement material known in the art, including, but not limited to use of: a grommet, an eyelet, stitching, and rivets, or any combination thereof. In a preferred embodiment, the reinforcement material may be a silver colored printed silicon. In another embodiment the reinforcement material may be a reflective or a non-reflective plastic material.

BRIEF DESCRIPTION OF THE DRAWINGS

The description of the various example embodiments is explained in conjunction with appended drawings, in which:

FIG. 5 is a front view of the therapeutic shirt of FIGS. 1-4, showing regions where higher compression materials are located on the primary layer, and showing the locations of the openings into the pockets, and the shape and extent of the pockets;

FIG. 6 is a cross-sectional view through one of the pockets of the therapeutic shirt of FIG. 5, shown prior to inserting of a heat/cold pack therein;

FIG. 6A is a cross-sectional view through one of the pockets of the therapeutic shirt, but where the pocket is constructed differently than the pocket shown in FIG. 6, as it does not utilize a liner, and is also shown prior to inserting of a heat/cold pack therein;

FIG. 7 is the cross-sectional view of FIG. 6, but shown after a heat/cold pack has been inserted into the pocket;

FIG. 7A is the cross-sectional view of FIG. 6A, but shown after a heat/cold pack has been inserted into the pocket;

DETAILED DESCRIPTION OF THE INVENTION

Figure 1:
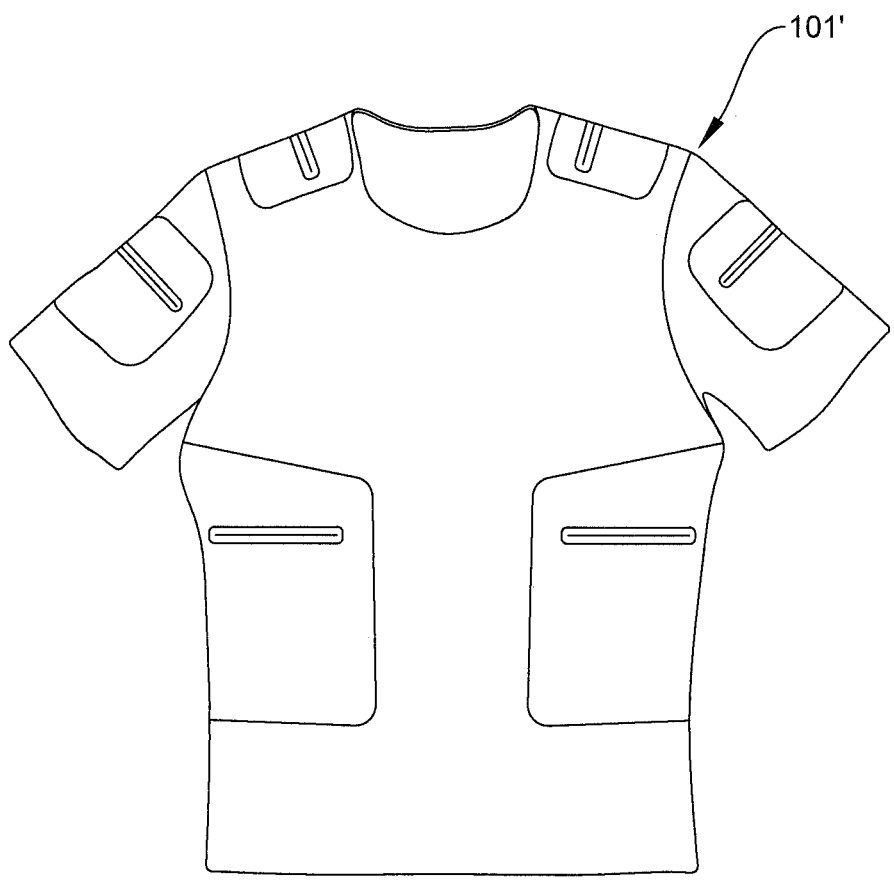
FIGS. 1-4 are front, top, side and rear views of a compression garment configured as a therapeutic shirt that applies heat and/or cold therapy to regions of a wearer's body.
Figure 2:
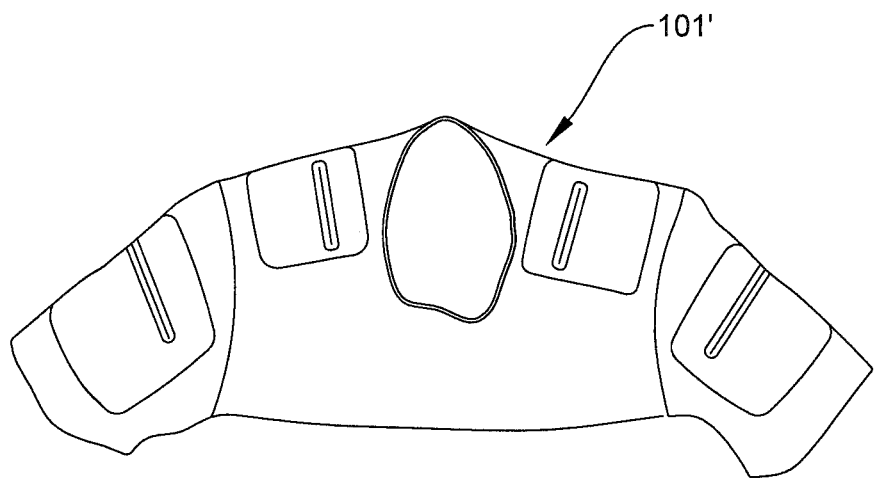
Figure 3:
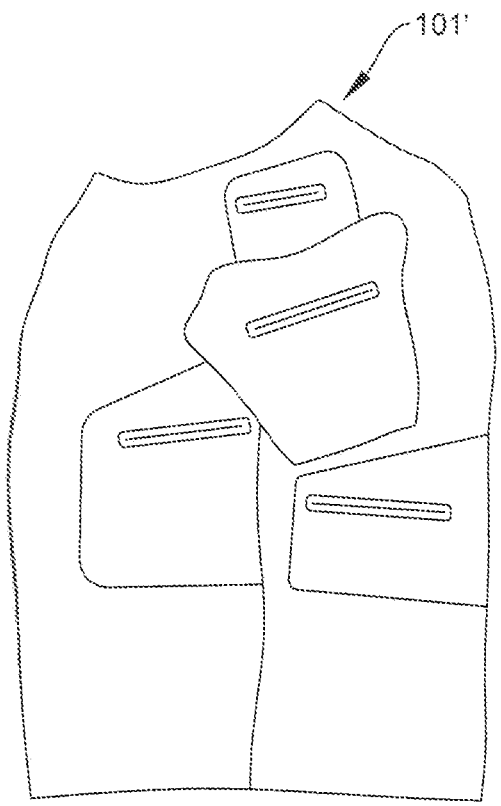
Figure 4:
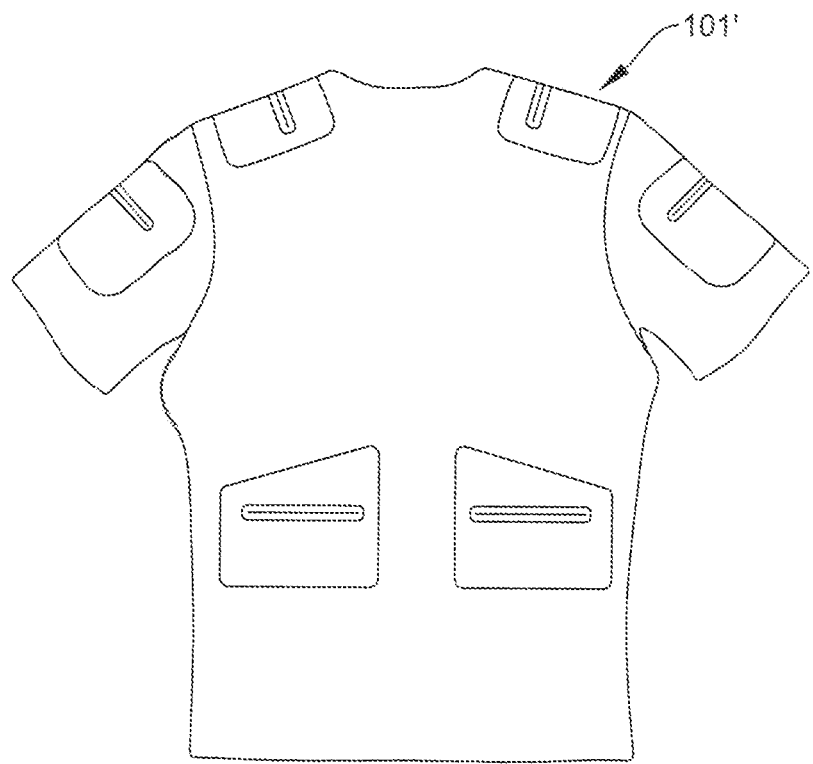

As used throughout this specification, the word "may" is used in a permissive sense (i.e., meaning having the potential to), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that citing herein of any patents, published patent applications, and non-patent literature is not an admission as to any of those references constituting prior art with respect to the disclosed apparatus.

Furthermore, the described features, advantages, and characteristics of any particular embodiment disclosed herein, may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related.

Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/feature being quantified.

Furthermore, a numerical difference provided by the approximating language may also correspond to an overall tolerance for the aspect/feature that may be derived from variations resulting from a stack up (i.e., the sum) of a multiplicity of such individual tolerances.

Any use of a friction fit (i.e., an interface fit) between two mating parts described herein indicates that the opening (e.g., a hole) is smaller than the part received therein (e.g., a shaft), which may be a slight interference in one embodiment in the range of 0.0001 inches to 0.0003 inches, or an interference of 0.0003 inches to 0.0007 inches in another embodiment, or an interference of 0.0007 inches to 0.0010 inches in yet another embodiment, or a combination of such ranges. Other values for the interference may also be used in different configurations (see e.g., "Press Fit Engineering and Design Calculator," available at: www.engineersedge.comn/calculators/machine-design/press-fit/press-fit-calculator.htm).

Any described use of a clearance fit indicates that the opening (e.g., a hole) is larger than the part received therein (e.g., a shaft), enabling the two parts to move (e.g. to slide and/or rotate) when assembled, where the gap between the opening and the part may depend upon the size of the part and the type of clearance fit—i.e., loose running, free running, easy running, close running, and sliding (e.g., for a 0.1250 inch shaft diameter the opening may be 0.1285 inches for a close running fit. and may be 0.1360 inches for a free running fit; for a 0.5000 inch diameter shaft the opening may be 0.5156 inches for a close running fit and may be 0.5312 inches for a free running fit). Other clearance amounts are used for other clearance types. See "Engineering Fit" at: https://en.wikipedia.org/wiki/Engineering_fit; and "Three General Types of Fit," available at www.mm-to.org/dclark/Reports/Encoder%20Upgrade/fittolerences%20%5BRead-Only%5D.pdf.

It is further noted that any use herein of relative terms such as "top," "bottom," "upper," "lower," "vertical," and "horizontal" are merely intended to be descriptive for the reader, and may be based on the depiction of those features within the figures for one particular position of the apparatus, and such terms are not intended to limit the orientation with which the disclosed apparatus may be utilized.

As seen in images of FIGS. 1-4, a garment for applying thermal treatments (heating or cooling) to one or more regions of a wearer's body may be formed into a therapeutic shirt 101' that may include a primary layer of material, a particularly shaped pocket that may be formed in one of several different ways, and a particularly located layer or layers of higher compression material that overlie or underlie a treatment region positioned beneath the pocket. The treatment region may be any portion of the human body, including, but not limited to, a rib or post-surgery treatment region 95, an elbow treatment region 96, a shoulder treatment region 97, a muscle treatment region 98, etc. (Note that the treatment areas may be larger than shown in FIG. 5, and the treatment region may be defined by the extend of the high compression material, or the extent of the heat/cold pack, or both).

The therapeutic shirt 101' may be symmetrical about its center line 101C, but need not be so made, as the treatment areas may be different for different sides of the body. Moreover, the therapeutic shirt 101' may be custom made to treat specific areas for a particular patient.

A front view of a therapeutic shirt 101 is shown in FIG. 5, which may be formed the same as the therapeutic shirt 101', but which may be formed as either a long sleeved shirt or a short sleeved shirt, and the figure illustrates both options therein (i.e., showing a short sleeve on one side and a long sleeve on the other side). The therapeutic shirt 101 may also be collarless.

The therapeutic shirt 101 includes a primary layer 110, being formed of a first material, such that an interior surface of the primary layer envelops a portion of the wearer's body (e.g., a portion of the torso from about the waist upwards, the shoulders, and at least a portion of the arms-see FIGS. 14-17), and which enveloped portion of the wearer's body includes the one or more regions to be treated thermally. The material of the primary layer 110 may be an elastic material that may include, but is not limited to, a spandex material, a stretch vinyl, polyester, bamboo, any blends of those materials, and any other suitable fabrics known in the art. The primary layer 110 being so formed may thus be configured for an interior surface to apply a first level of compression to those enveloped portions of the wearer's body. In one embodiment the elastic material 110 may exhibit a compression pressure in the range of 2 mm Hg to 5 mm Hg, and in another embodiment the elastic material may exhibit a compression pressure in the range of 5 mm Hg to 8 mm Hg, and in yet another embodiment the elastic material may exhibit a compression pressure in the range of 8 mm Hg to 11 mm Hg, and in another embodiment the elastic material may exhibit a compression pressure in the range of 11 mm Hg to 16 mm Hg, and in other embodiments other ranges or a combinations of those ranges may instead be used.

The therapeutic shirt 101 also includes one or more layers of a second material located at each region to be treated (e.g., layer(s) 120 for treating a rib region or post-surgery region 95; layer(s) 130 for treating an elbow region 96; layer(s) 140 for treating a shoulder region 97; layer(s) 150 for treating a muscle region 98; etc.). In one embodiment, only one layer of the material may be used at a treatment region, and in another embodiment two layers of the material may be used at a treatment region, and in yet another embodiment three layers of the material may be used at a treatment region, while other numbers of layers may be used in other embodiments.

The one or more layers of the second material, e.g., layer(s) 120, may be a high compression material that may include, but is not limited to: a thermoplastic elastomer (TPE), a polyurethane, and any other suitable material known in the art.

Where three layers of the compression material are used (e.g., layers 120i, 120ii, and 120iii—see FIG. 6), an innermost compression layer (e.g., layer 120i) may be the closest of those layers to the skin of the wearer, an outermost layer (e.g., layer 120iii) may be the farthest away from the skin of the three layers, and the middle layer (e.g., layer 120ii) may be positioned between the other two layers. One or more of those layers may be a mesh, and where three layers are used, the middle layer is preferably a mesh.

The layer or layers of the second material (e.g., layer 120 or layers 120i, 120ii, and 120iii), which layers may be stacked and coextensive, may be fixedly secured to the primary layer 110 on its interior (or exterior) surface in any suitable manner (e.g., stitching), and each may be shaped to overlay and extend beyond the treatment region of the wearer's body. The second material of the one or more layers may be a compression material configured to apply a second level of compression being greater than the first level of compression applied by the elastic material of the primary layer 110. In one embodiment this higher compression material may be formed to exhibit a compression pressure in the range of 20 mm Hg to 35 mm Hg, and in another embodiment the high compression material may exhibit a compression pressure in the range of 35 mm Hg to 50 mm Hg, and in yet another embodiment the high compression material may exhibit a compression pressure in the range of 50 mm Hg to 65 mm Hg, and in another embodiment the high compression material may exhibit a compression pressure in the range of 65 mm Hg to 88 mm Hg, and in other embodiments other ranges or a combinations of those ranges may instead be used.

In one embodiment, the elastic material of the primary layer 110 may have an opening formed proximate to each treatment region but away from the layer(s) of high compression material, and the heat/cold packs may ultimately be positioned between a liner 125 and the layer(s) of high compression material when in use (see e.g., FIG. 6 and FIG. 7).

Figure 11:
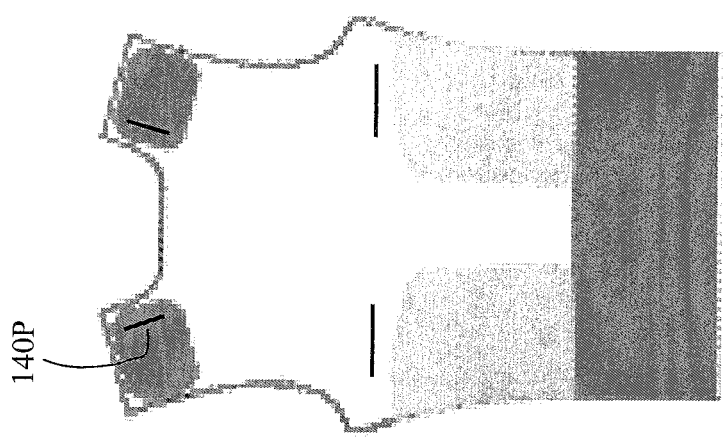
FIGS. 10-11 are views of the flat patterns of the front side, sleeves, and a rear side that may be used to make the therapeutic shirt of FIGS. 1-4, and which also show a second series of locations for high compression material(s)

In another embodiment, the elastic material of the primary layer 110 may have an opening formed proximate to each treatment region that overlies the layer(s) of high compression material, and the heat/cold packs may ultimately be positioned between the primary layer 110 and the layer(s) of high compression material when in use (see opening 140P in FIG. 11; and see the pockets in FIG. 5, FIG. 6A and FIG. 7A).

In either embodiment, the opening may be sized to admit the width of either a heat pack 80H or a cold pack 80C therethrough, which heat packs and cold packs may be the same or similarly sized. For example, an opening 110P may be formed in the elastic material of the primary layer 110 just above the one or more layers 120, as seen in FIG. 5. Note that the opening 110P and the other openings are shown with a large gap in FIG. 5, and may instead be formed to be much smaller; in fact, each of the openings including opening 110P may instead be formed as a slit. The opening 110P may be formed in the elastic material of the primary layer 110 just above the one or more layers 120 (i.e., as shown in FIGS. 5, 6, and 7) for a number of reasons:

1. The slit is just above the high compression regions because having the heat/cold pack positioned within the pocket, being completely overlaid by the high compression materials and away from the slit that locally reduces the compression force, subjects the pack to a uniform compression force that forces the pack into contact with the wearer's skin, greatly increases both the efficiency of the heat/cold pack and the effectiveness of the thermal therapy provided by the heat/cold pack. See e.g., Prawit Janwantanakul, "Cold Pack/Skin Interface Temperature during Ice Treatment with Various Levels of Compression," Physiotherapy, Vol. 92, Issue 4, December 2006, Pages 254-259.
2. The slit is just above the high compression regions because the size of the ice/heat packs are just as specific to that location and region of the body. Be it how long the body should be cooled there, or that a said region has less fat cells and thus gets cooler or hotter quicker, or a region has more fat cells and will insulate the cold or heat longer.
3. Because the ice/heat packs utilized herein are not as large as many of the prior art ice/heat packs; the packs utilized herein are about 100% to 400% less grams but are able to get hotter or colder quicker.
4. By positioning the heat/cold packs completely beneath the high compression materials they become far more effective in targeting the correct areas that need the thermal therapy, which is important because the herein disclosed packs do not need to get as cold or as hot as the other heat/cold packs used in prior art compression garments.
5. By having the compression materials directly above the pocket location that stores the heat/cold pack, we use: the strength of the compression×the size of the pocket× the volume of the packs×the location on the body+ knowing the change in body temperature in a region should be controlled to be most effective. Anywhere from 5 to 11 degrees C. change in external skin temperature is the perfect variation to aid the connective tissues, muscles, joint regions, etc. etc. By this theory, the packs utilized herein do not need to get as cold or as hot as the others in the market —because the formula is factoring all the above into effectively maintaining the correct regional temperature for either the heating or cooling effect that is required.
6. The temperature above can be marginally adjusted 2 to 5 degrees C. by just raising or cooling the packs a mere 1.5 degrees.
7. The slit is therefore just outside the high compression region (top, side, bottom) to target and insolate the adjusted temperature effect (Note—the slit can be located centrally on the high compression materials (i.e. directly on top of the heat/cold packs) and the packs may be push through the slit, but which is somewhat less effective).
8. The other region that the slits are here—is the packs when at room temperature $2^{nd}$ as a target, shape specific added compression for the body—if the patient or the customer is in need of that For the embodiment shown in FIGS. 5, 6 and 7, a liner (e.g. liner 125) may be fixedly secured to the arrangement to create a selectively shaped pocket. A first portion 125i of a periphery of the liner 125 may be fixedly secured (e.g., stitched) to the interior surface of the primary layer 110 such that it may extend over the opening 110P, and a second portion 125ii of a periphery of the liner 125 may extend over only a portion of a periphery of the one or more layers of high compression material (e.g., layer 120), and is secured to the one or more layers to form a pocket. The interior of the pocket may be selectively shaped to receive the correspondingly shaped heat/cold pack therein, as discussed hereinafter. In one embodiment, as shown for the left-side pocket in FIG. 5 (the pocket on the right side when looking at the figure), the upper portion of the liner 125 may be coterminous with the extent of the left and right sides and the top of the opening 110P, and the liner may be secured (e.g., stitched) thereto. In another embodiment, as shown for the other pocket in FIG. 5, the liner 125' may be wider than the extent of the left and right sides of the opening 110P, and may also extend above the top of the opening 110P, and may be secured thereat.

FIG. 6 shows a cross-sectional view through a first one of the pockets of the therapeutic shirt 101 of FIG. 5, shown prior to inserting of a heat pack 80H or a cold pack 80C therein, while FIG. 7 is that cross-sectional view of FIG. 6, shown after a heat/cold pack has been inserted into the pocket.

Positioning the opening HOP in the elastic material of the primary layer 110 and not in proximity to the high compression material layer(s) 120 may make it easier to initiate installing of the heat/cold packs 80H/80C into the pocket from the outside while the shirt 101 is being worn.

In addition, to further accommodate ease of installing of the heat/cold packs 80H/80C into the pocket in one embodiment the liner 125/125' may be made of the same elastic material used for the primary layer 110. Since the liner 125/125' is preferably more conducive to transmitting heat/ cold therethrough, in another embodiment the liner 125/125' is preferably made of a thinner elastic material than the elastic material of the primary layer 110, and may be only a slightly elastic material (e.g., it may exhibit a compression pressure in the range of 1 mm Hg to 5 mm Hg). In another embodiment the liner 125/125' may be made of a light to medium weight cotton fabric that may be slightly oversized for holding the heat/cold packs 80H/80C, or instead of being oversized, cotton blends thereof may be used that may include blends with elastic fibers. In one embodiment the liner may be made of nylon and spandex, and may be made of a base of at least 76-80 percent nylon, with the rest spandex.

To permit further ease of installing the heat/cold packs into the opening 110P, the heat/cold packs 80H/80C may be shaped like a gonfalon flag, having an elongated rectangular body that transitions into a triangular shape with a tip that may be centrally positioned (see FIG. 5) and which tip may be slightly rounded. The tip of the gonfalon shaped heat/cold packs 80H/80C may first be inserted into the pocket to establish some clearance between the liner and the high compression layers, prior to the entirety of the width of its heat/cold pack body being slowly inserted through the opening 110P. The tip of the gonfalon shape of the heat/cold packs 80H/80C may ultimately be positioned at a bottom of the pocket, which pocket may be correspondingly shaped (i.e., the interior of the pocket may also have a gonfalon shape that may be slightly larger than the periphery of the heat/cold pack received therein). Each of the corners of the heat/cold packs 80H/80C may also be rounded.

Heat and cold packs are generally known in the art, as shown for example by the following U.S. Patents: U.S. Pat. No. 2,907,173 to Robbins; U.S. Pat. No. 3,175,558 to Caillouette; U.S. Pat. No. 3,342,324 to Piazze; U.S. Pat. No. 3,542,032 to Spencer; U.S. Pat. No. 3,804,077 to Williams; U.S. Pat. No. 4,462,224 to Dunshee; U.S. Pat. No. 5,792,213 to Bowen; U.S. Pat. No. 3,889,684 to Lebold; U.S. Pat. No. 4,462,224 to Dunshee; U.S. Pat. No. 4,700,706 to Munch; U.S. Pat. No. 5,190,033 to Johnson; and U.S. Pat. No. 5,843,145 to Brink.

In the embodiment with the custom heat/cold packs 80H/80C being positioned beneath the high compression layer or layers (e.g., beneath layers 120i, 120ii, and 120iii), the compressive force of those layers force the heat/cold packs into contact with the wearer's skin surface to be treated, making them more effective, and permits the use of smaller heat/cold packs.

The repeated insertion of the custom heat/cold packs 80H/80C through the opening 110P may tend to cause wear, and possibly fraying and tearing of the elastic material at the opening. Therefore, in one embodiment a reinforcement material 111 may positioned around a periphery of the opening 110P in the primary layer 110, and may be suitably secured thereto. In different embodiments, the reinforcement material used may be one or more rivets, an eyelet, a grommet, stitching, or any combination of those reinforcement materials. In another embodiment, the reinforcement material may be a silver colored printed silicon. In another embodiment the reinforcement material may be a reflective or a non-reflective plastic material.

Figure 10:
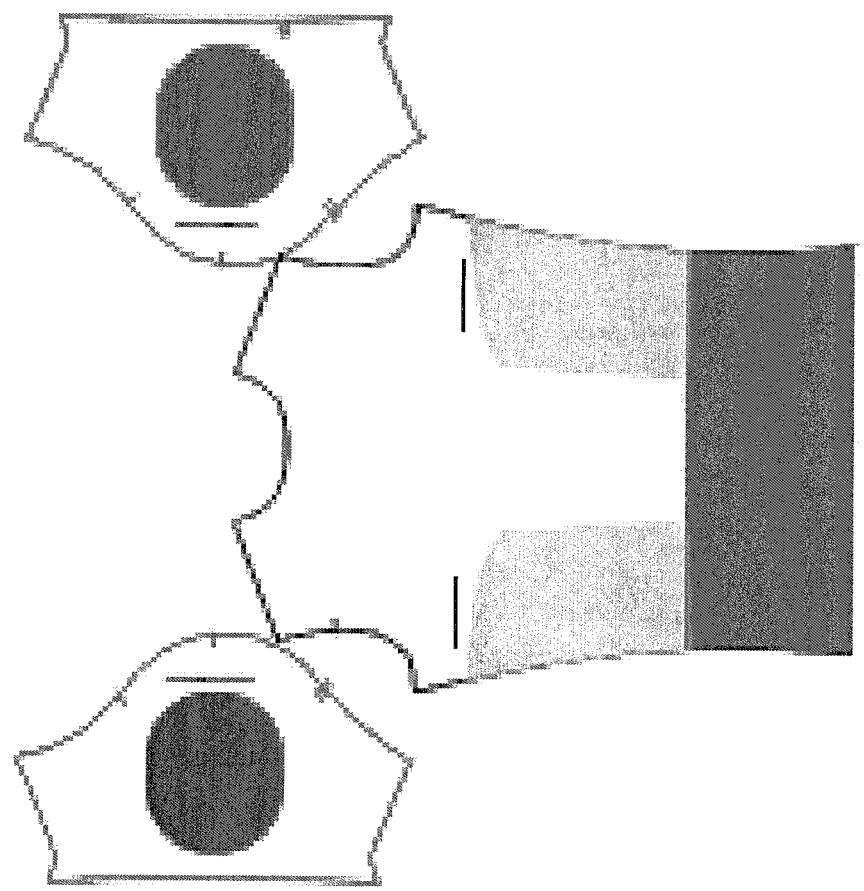

The therapeutic shirt formed by the flat patterns shown in FIG. 10 and FIG. 11, having a full band of compression material proximate to the waist (e.g., a low compression material in the front shown in FIG. 10 and a high compression material in the back shown in FIG. 11), may also serve to reduce certain types of hernias.

Figure 13:
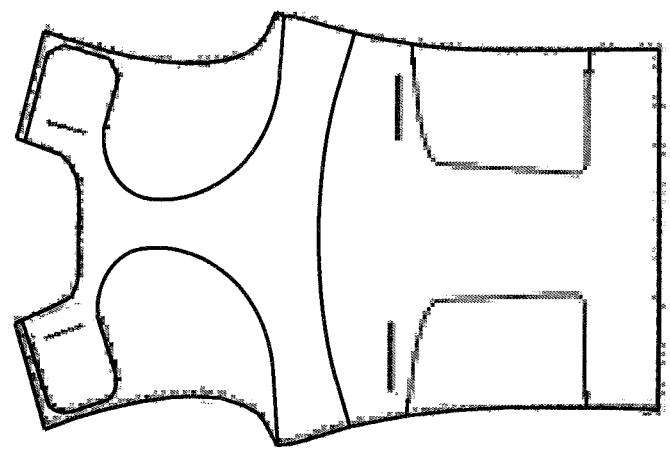
FIGS. 12-13 are views of the flat patterns of the front side, sleeves, and rear side that may be used to make the therapeutic shirt of FIGS. 1-4, showing a third series of locations for high compression material, and where the pockets may be positioned in the high compression material.
Figure 12:
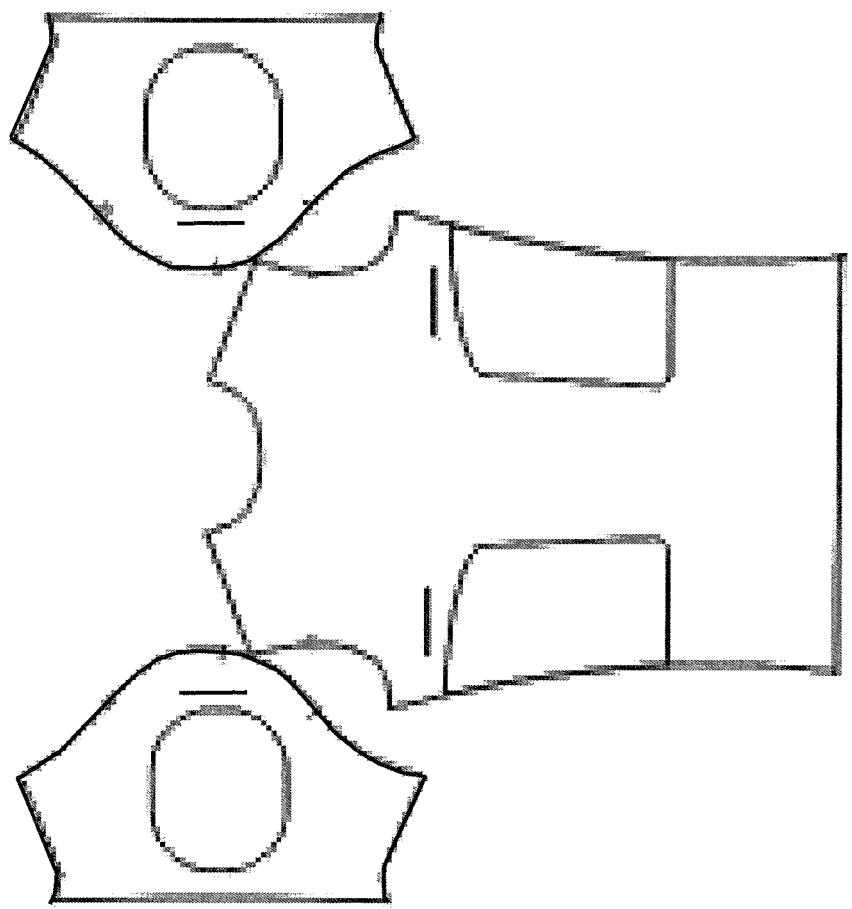
Figure 14:
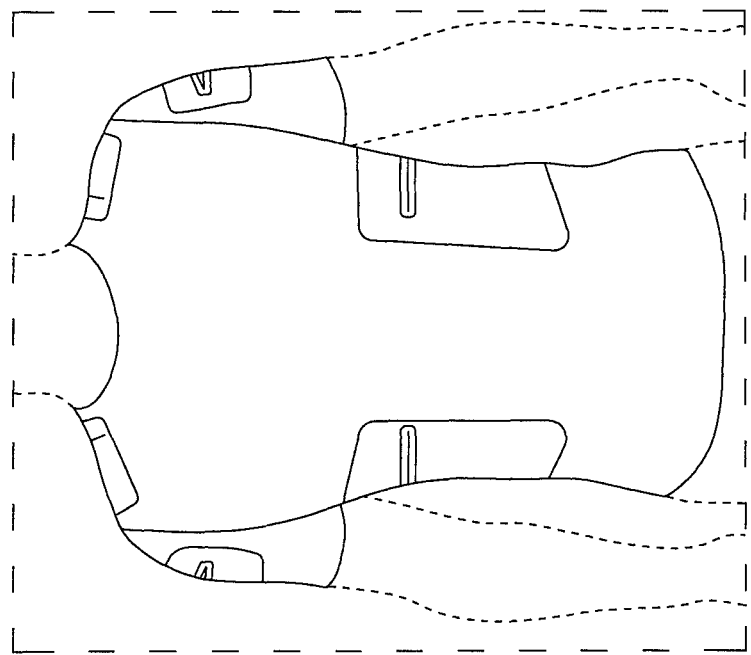
FIG. 14 is a front view of the compression garment of FIGS. 1-4 shown after being donned by a person.
Figure 15:
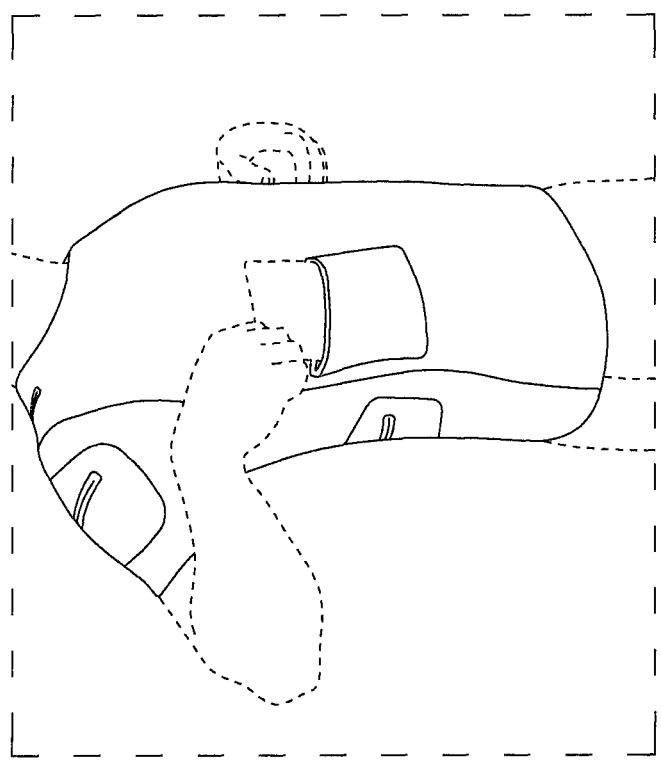
FIG. 15 is a view of the right front portion of the compression garment of FIG. 14, shown with the person inserting a heat/cold pack into the right front pocket.
Figure 17:
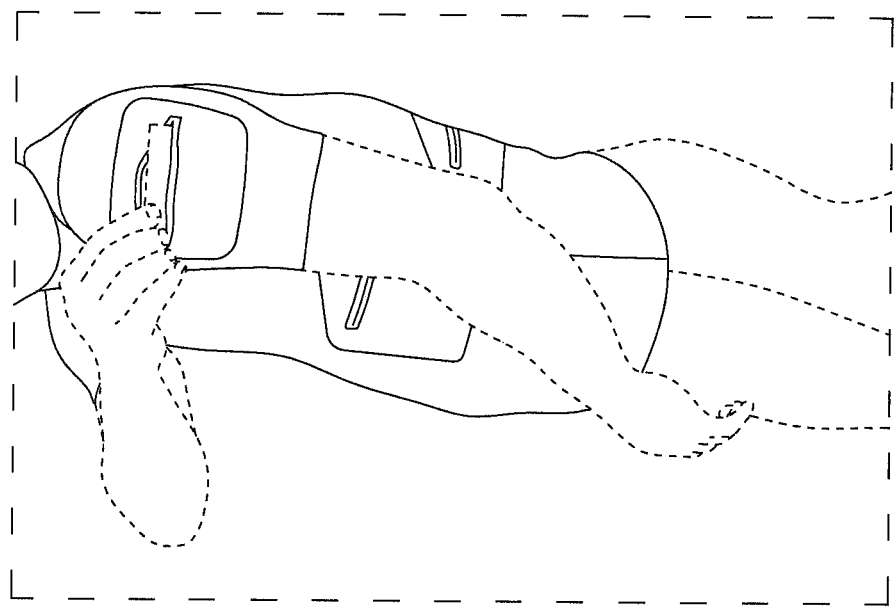
FIG. 17 is the left side view of FIG. 16, shown with the person inserting a heat/cold pack into the left shoulder pocket.
Figure 16:
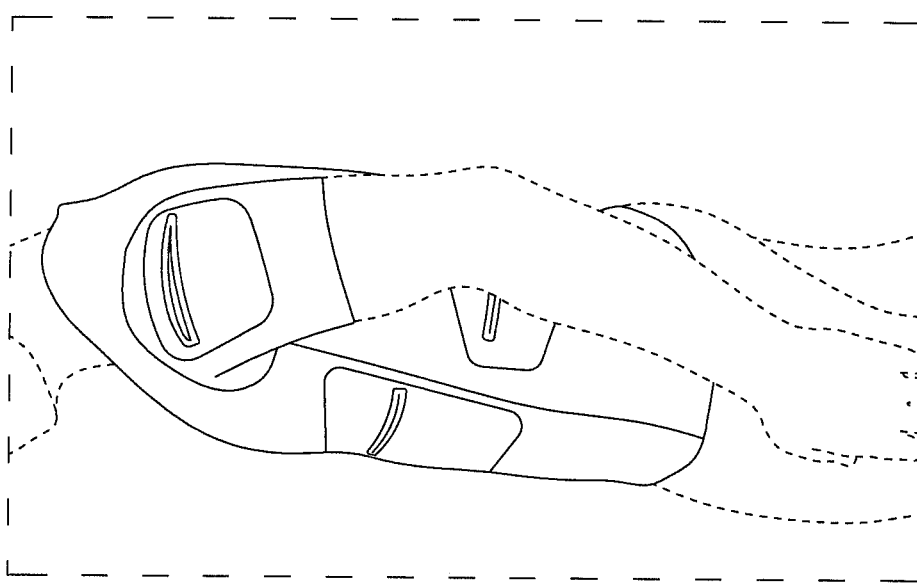
FIG. 16 is a left side view of the compression garment of FIGS. 1-4 shown after being donned by a person.
Figure 18A:
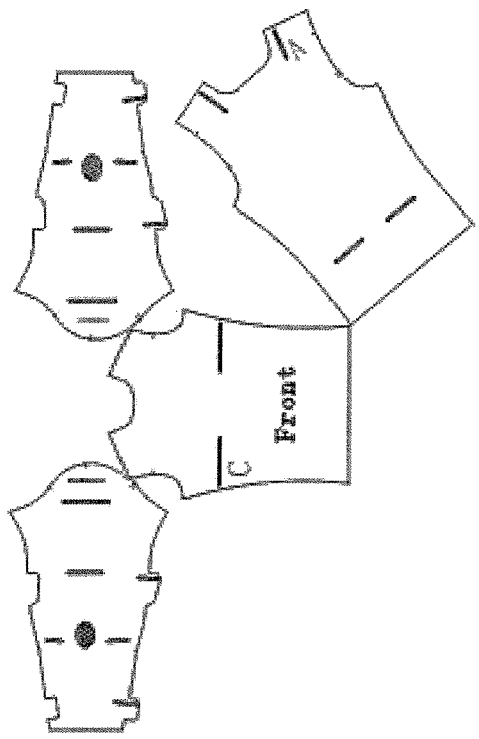
FIG. 18A illustrates views of flat patterns of the front side, sleeves, and rear side that may be used to make the therapeutic shirt of FIG. 18, showing locations of the opening into the pockets.
Figure 18B:
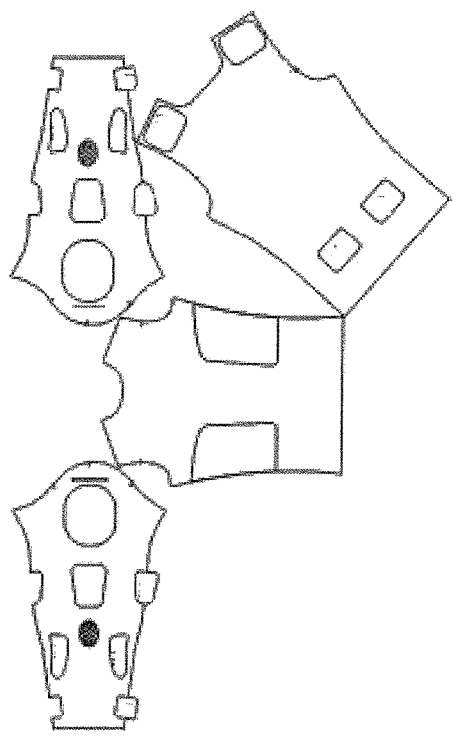
FIG. 18B illustrates views of flat patterns of the front side, sleeves, and rear side that may be used to make the therapeutic shirt of FIG. 18, showing a first set of locations for high compression materials.
Figure 18:
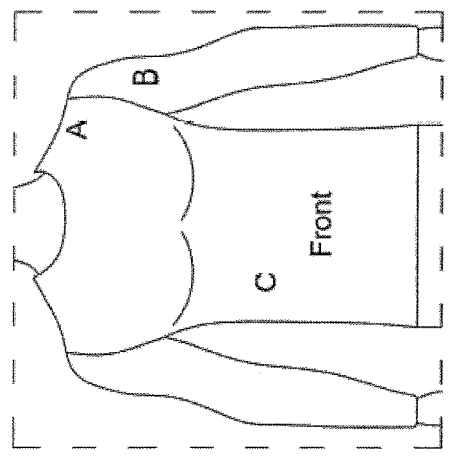
FIG. 18 is a front view of a long sleeve compression garment configured as a therapeutic shirt for use by an athlete, particularly a football player.
Figure 18C:
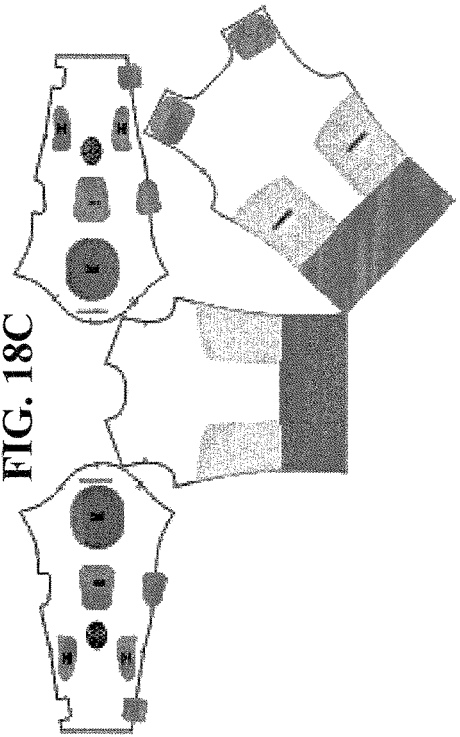
FIG. 18C illustrates views of flat patterns of the front side, sleeves, and rear side that may be used to make the therapeutic shirt of FIG. 18, showing a second set of locations for high compression materials.

As seen in FIG. 13, one or all of the layers of high compression materials may also be continuous around an upper part of the body.

Figure 5A:
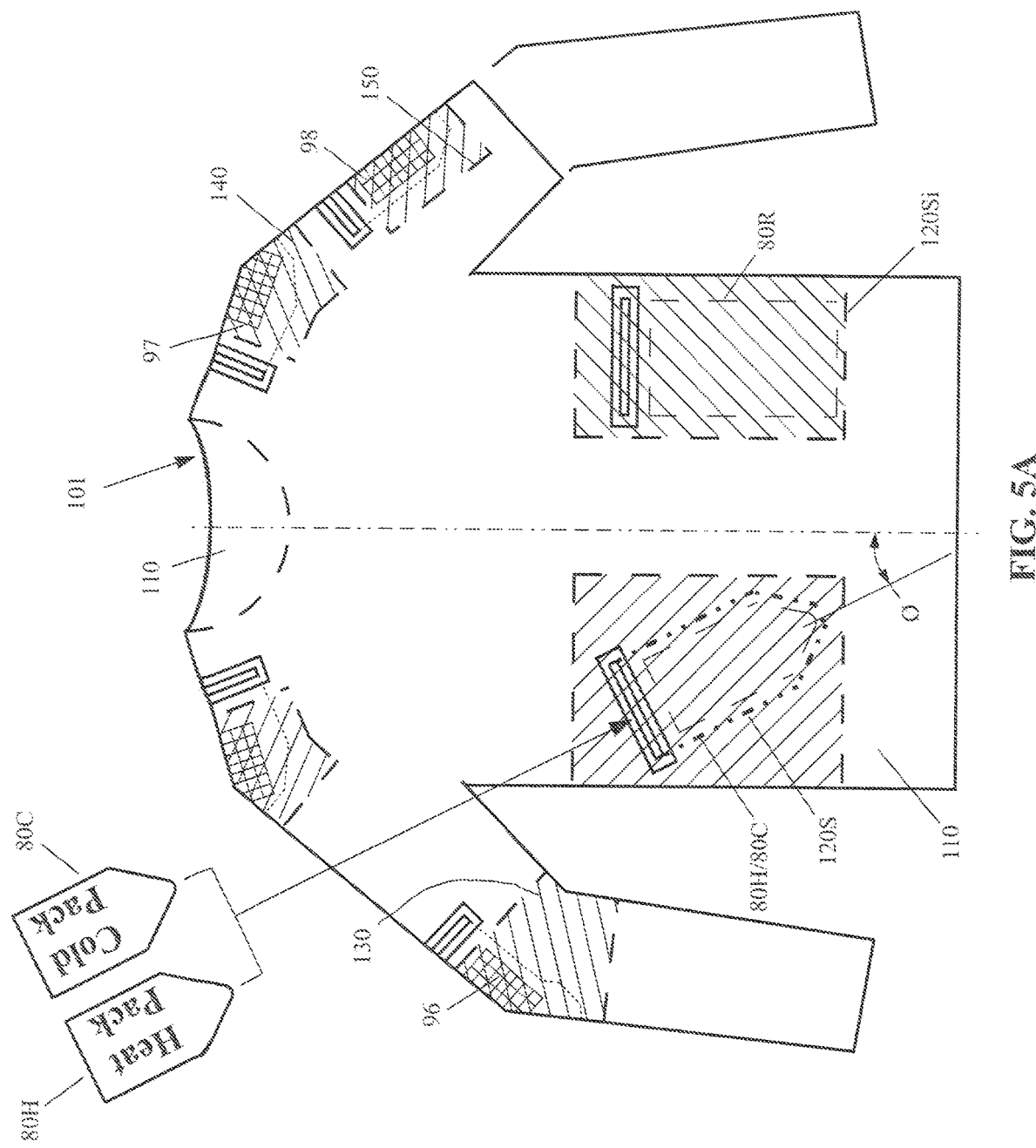
FIG. 5A is a rear view of the therapeutic shirt of FIG. 5.
Figure 9:
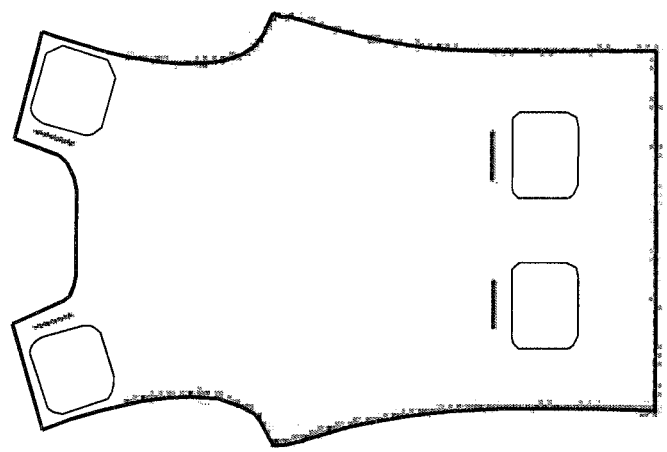
FIGS. 8-9 are views of flat patterns of a front side, sleeves, and a rear side that may be used to make the therapeutic shirt of FIGS. 1-4, and showing a series of locations for high compression material(s)
Figure 8:
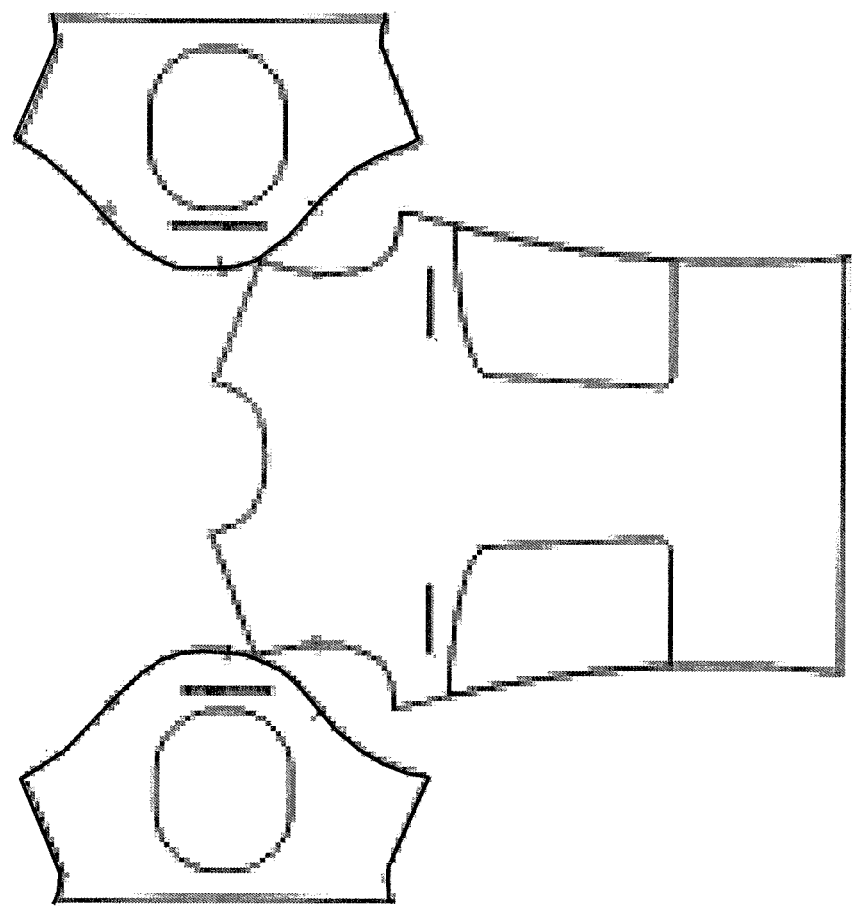

As seen in FIG. 5A, each of the pockets on the rear of the shirt may be angled towards the mid-plane of the shirt, which makes it easier for the user to insert the heat/cold packs into the pocket while wearing the shirt, and reaching an arm around his/her back. The axis of the pocket may be at an angle θ with respect to vertical (i.e., with respect the centerline of the shirt) being in the range of 15 degrees to 35 degrees in one embodiment, or in the range of 35 degrees to 55 degrees in another embodiment, or in the range of 55 degrees to 75 degrees in yet another embodiment, or a combination of these ranges or other ranges may be used in other embodiments.

The primary layer 110 may be secured (e.g., using stitching 120S) to the one or more layers of high compression material (e.g., layer 120) to form the periphery of the interior of the pocket. Note that as shown for the right rear pocket in FIG. 5A, a rectangular hot/cold pack 80R may be used, and may be received in the rectangular interior of the pocket that may be formed by stitching 120Si at the periphery of the one or more layers of high compression material.

While illustrative implementations of one or more embodiments of the disclosed apparatus are provided hereinabove, those skilled in the art and having the benefit of the present disclosure will appreciate that further embodiments may be implemented with various changes within the scope of the disclosed apparatus. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. A garment, said garment configured to selectively apply compression therapy and thermal therapy to one or more treatment regions of a wearer's body, said garment comprising: a primary layer of a first material configured to form a shirt, with an interior surface of said shirt configured to envelop and contact a portion of the wearer's upper body including the torso from about the waist upwards, the shoulders, at least a portion of the arms, and the one or more treatment regions, said first material of said primary layer consisting of an elastic material configured for said interior surface to apply a first level of compression to said portion of the wearer's upper body; wherein said primary layer is configured to form an outer surface of said garment; one or more interior spaces with an opening in said primary layer to provide access to each said interior space; wherein the one or more interior spaces are configured to overlie each of the one or more treatment regions of the wearer's body, respectively, each said interior space comprising a periphery configured to correspond to at least a portion of a periphery of a heat/cold pack received therein; wherein each said opening is positioned proximate to the one or more treatment regions of the wearer's body; and one or more layers of a second material, with each of said one or more layers of the second material having at least a respective periphery fixedly secured to said primary layer, and each of said one or more layers of the second material being configured to respectively overlie and extend beyond the one or more treatment regions of the wearer's body and beyond each of said one or more interior spaces, said one or more layers of the second material each comprising a compression material configured to apply a second level of compression; wherein said second level of compression is greater than said first level of compression; and wherein said periphery of each said interior space comprising a gonfalon shape configured to correspond to a periphery of the heat/cold pack, with a tip of said gonfalon shape of said periphery of said interior space positioned at a bottom of said interior space; wherein said gonfalon shape of said periphery of said interior space comprises: an elongated rectangular shape that transitions into a triangular shape, with a tip of said triangular shape being centrally positioned; and further comprising a liner for each said interior space, a first portion of a periphery of said liner being fixedly secured to said primary layer with said first portion of said liner configured to extend over said opening, and a second portion of said periphery of said liner configured to extend over only a portion of a periphery of said one or more layers of the second material, and be secured to said only a portion of said periphery of said one or more layers, to form each said interior space.

2. The garment according to claim 1 wherein said opening is positioned in said primary layer of the first material proximate to but at a distance away from said one or more layers of the second material.

3. The garment according to claim 1 wherein said opening is positioned in said primary layer of the first material to overlie said one or more layers of the second material.

4. The garment according to claim 1, wherein said opening comprises an elongated slit.

5. The garment according to claim 4 further comprising: a reinforcement material positioned around a periphery of said elongated slit.

6. The garment according to claim 5 wherein said reinforcement material comprises printed silicon material.

7. The garment according to claim 5 wherein said reinforcement material comprises a reflective plastic material.

8. The garment according to claim 5 wherein said reinforcement material comprises a non-reflective plastic material.

9. The garment according to claim 5 wherein said reinforcement material comprises one or more rivets.

10. The garment according to claim 5 wherein said reinforcement material comprises an eyelet.

11. The garment according to claim 5 wherein said reinforcement material comprises a grommet.

12. The garment according to claim 5 wherein said reinforcement material comprises stitching.

13. The garment according to claim 4 further comprising: means for reinforcing a periphery of said elongated slit.

14. The garment according to claim 1 wherein said one or more layers of the second material are formed of three layers of the second material, said three layers comprising an innermost layer, a middle layer, and an outermost layer.

15. The garment according to claim 14,
wherein said primary layer of elastic material is selected from a group of elastic materials consisting of: a spandex material, a polyester blend, and a bamboo blend.

16. The garment according to claim 15 wherein said compression material is selected from a group of compression materials consisting of: a thermoplastic elastomer (TPE), and a polyurethane.

17. The garment according to claim 1, wherein said tip of said gonfalon shape of said interior of said pocket is rounded.

\* \* \* \* \*